United States Patent [19]

Smith et al.

[11] Patent Number: 5,171,581
[45] Date of Patent: Dec. 15, 1992

[54] METHOD AND COMPOSITION FOR TREATING PSORIASIS

[76] Inventors: Steven A. Smith; Lorraine J. Smith, both of 5706 S. 30th W. Ave., Tulsa, Okla. 74107

[21] Appl. No.: 518,170

[22] Filed: May 1, 1990

[51] Int. Cl.$^5$ .................. A61K 33/24; A61K 31/28
[52] U.S. Cl. .................. 424/617; 424/404; 514/501; 514/863; 514/192; 514/250; 420/441; 423/493
[58] Field of Search .............. 514/501, 863; 424/617; 420/441; 423/493

[56] References Cited

PUBLICATIONS

4, *Monthly Cyclopaedia & Medical Bulletin*, pp. 348–355,
"On The Uses of Nickel Sulphate in Medicine" by Louis Kolipinski, M.D. (1911).
The Merck Index, Windholz et al. editor, 10th Edition Merck & Co. Inc., Rathway NJ, 1983 pp. 932.
Weingartner et al. "Composition of the First . . . in Conc. Aqueous $NiCl_2$ and $NiBr_2$ solutions". J. Chem. Soc., Faraday Trans. 1, 75 (12), 2700–11.

*Primary Examiner*—Richard L. Raymond
*Assistant Examiner*—B. Bembenick
*Attorney, Agent, or Firm*—Steinberg & Raskin

[57] ABSTRACT

Psoriasis molecules are treated by administering non-toxic pharmaceutically acceptable solutions (topically, orally or by I.V.) of a composition containing nickel with a bromide carrier.

23 Claims, 1 Drawing Sheet

METHOD AND COMPOSITION FOR TREATING PSORIASIS

BACKGROUND OF THE INVENTION

Psoriasis is a chronic skin disorder that is proliferative in nature and widespread throughout the world, afflicting millions of humans and even domesticated animals having similar proliferative integument problems. The skin disorder is characterized by recurrent, elevated red lesions, plaques or rarely pustules on the skin. These plaques are the result of an excessive by rapid growth and shedding of epidermal (skin) cells.

No one knows what causes this abnormal cell proliferation. Its severity and course vary greatly from case to case, and also in the individual afflicted with the disease. Recurrences are almost the rule with intervals varying from one month to many years. One person may go through life with a single patch on the elbow, knee or scalp, while another will have repeated attacks of a qeneralized eruption or widespread chronic lesions lasting for years without remission. As discouraging as it may be, medical science and literature are replete with indications that patients exhibiting such lesions are destined for life to be "psoriatic." With all of the advances in medical science, no one knows what causes this abnormal cell proliferation. With some of it, it is felt that some type of biochemical stimulus triggers this abnormal cell growth. It is still unknown whether the origin of this biochemical malfunction resides in the skin, in the immune system, in the white blood cells, or is possibly psycho-neural. It is known that certain environmental factors can "trigger" the initial appearance or worsening of psoriasis. Conversely, the symptoms can spontaneously clear for reasons scientists do not understand. Treatment of the psoriasis is aimed at clearing the lesions for as long as possible. This is what is meant by the term "remission" or "clearance." In any event, medical science has fairly well agreed that psoriasis is an heritable disease in which the specific defect seems to be unknown.

For years there have been many attempts to treat the disease, and several topical and systemic treatments for psoriasis which inhibit cell division have been with limited success in clearing the skin for short periods of time. Yet, the reason why these treatments work is not yet clearly understood. Treatments which have been suggested in the art appear to be symptomatic and palliative. Lesions may disappear spontaneously or as a result of the therapy, but recurrences are likely. There is a tendency for each remedy gradually to lose its effectiveness or develop dangerous accumulative toxicity. Rarely, however, is the disease apparently cured, showing no evidence for years.

In the treatment of the disease, medical science has suggested low fat or low protein diets. Drugs such as systemic corticosteroids and ACTH are effective but limited to patients who are in great distress and do not respond to other measures. Such drugs may produce dangerous side effects; and in some instances, once the drugs are discontinued, the eruption may show a marked exacerbation. Folic acid antagonists have been found to have some beneficial treatment but are a dangerous form of therapy. Although other drugs have been suggested, for the most part the serious side effects associated therewith have not made them successful. Ionizing radiation therapy, e.g. grenz-ray treatment has provided only temporary benefit, but the danger of addiction to such radiation producing radiodermatitis and subsequent carcinoma is not worth continued treatment. Corticosteroid ointment in combination with polyethylene film has had some success, but systemic effects may be caused by extensive use. Ointments have been found to be more beneficial than lotions. A typical ointment may contain anthralin or tar. Hydrophilic ointment containing salicylic acid and sulfur is also found to be beneficial, especially for scalp treatment. Here again, the side effects and the absorption within the human system, of these chemicals must be guarded. Other treatments including sunlight baths or ultraviolet (UV) baths, with the lesions painted with a solution of coal tar, anthralin or psoralens have been found to be helpful.

Ongoing studies in the art concern the use of Vitamin $D_3$, (1,25-dihydroxivitamin $D_3$). Etretin and Etretinate are new generation retinoids presently being studied for treating psoriasis, but again, the side effects must be carefully monitored.

Other ongoing studies include the use of the drug cyclosporine, RS 53179 (a non-steroidal, anti-inflammatory drug), fish oil, hypothermia, and anti-yeast agents.

One method for alleviating psoriasis is taught in U.S. Pat. No. 4,181,725 which teaches a pharmaceutical compound which contains as its active components at least one compound selected from the group consisting of parabromophenacyl bromide, alpha tocopherol, mepacrine, chloroquine, hydroxychloroquine, dibucaine, tetracaine, lidocaine, butacaine, procaine, ethylene diamine tetra, acetic acid, and ethylene glycol bis ($\beta$amino ethyl ether) -N-N'tetracetic acid within a suitable carrier.

SUMMARY OF THE INVENTION

Briefly, the present invention is directed to and encompasses as its object to provide methods and composition for the topical, oral, or intravenous treatment of psoriasis. Although the invention is primarily directed to psoriasis as the most serious of the skin diseases, other diseases such as dyshidrotic eczema, atopic dermatitides, primary irritant contact dermatitis, allergic contact dermatitis, lamellar ichthyosis, epidermolytic hyperkeratosis, seborrheic dermatitis in humans, and certain forms of dermatitis and mange in domesticated animals and psoriatic arthritis may benefit.

It is believed that there is are specific defective enzyme(s) in humans that are genetically predisposed to psoriasis. Certain exacerbating factors (lithium, stress, etc.) interfere with the function of such enzyme(s). It is believed this leads to a buildup of a metabolically active "psoriasis molecule(s)" which in turn either directly or indirectly triggers inflammation in the skin and/or joints. It is believed that the hematopoietic system (especially leukocytes) is the most likely source and most prolific producer of the "psoriasis molecules." A hepatic enzyme(s) probably compounds the problem by failing to catabolize and/or excrete this molecule(s). A defective kidney enzyme(s) may also play a role.

Specifically, this invention proposes and has for its object the use of bromide and nickel, either together as a single compound and/or separately in topical and/or oral processes which favorably affect the aforementioned enzyme(s) in people predisposed to psoriasis.

The invention is directed to a method of catabolizing the psoriasis molecule (P.M.) into a less toxic and/or excretable molecule by administering a composition of a non-toxic pharmaceutically acceptable amount of Nickel (Ni) into subcellular organelles of a human or animal cell which contain P.M. This is best accomplished using a carrier containing Bromide (Br). Pharmaceutically acceptable Nickel dibromide ($NiBr_2$) in an aqueous or saline solution or in tablet or capsule form has been found to be an acceptable compound for treatment of this viscious disease.

DETAILED DESCRIPTION AND EXAMPLES

Figure 1:
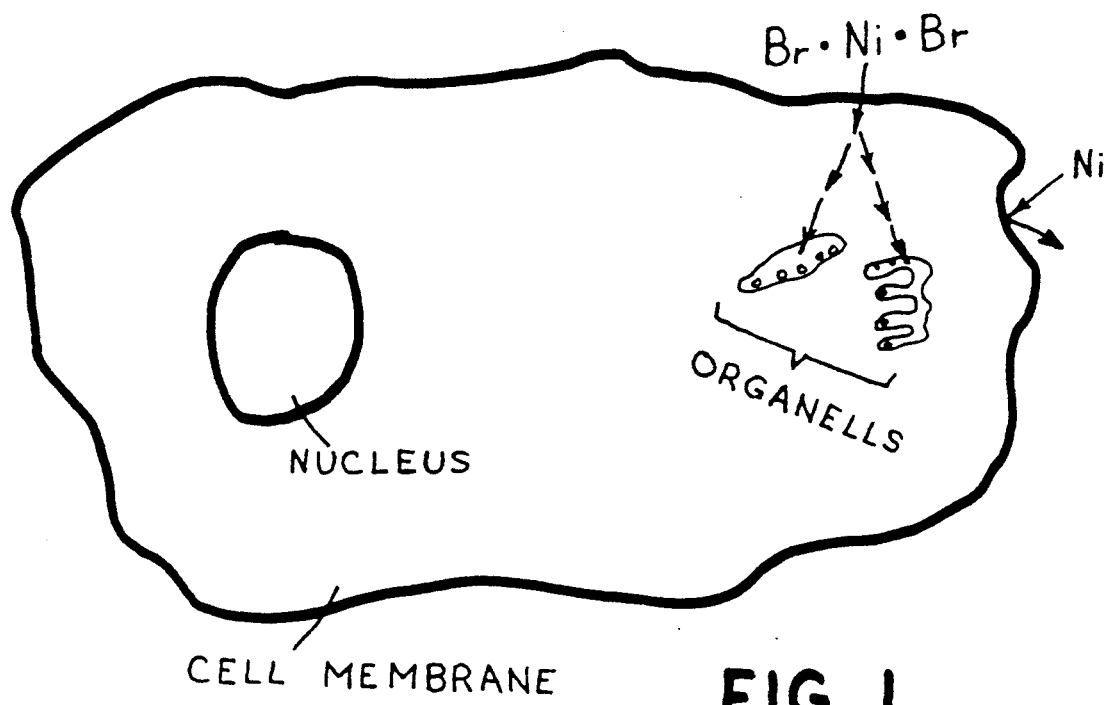
FIG. 1 is a diagrammatic view of the concepts of the invention in modifying a human cell.

Referring now to FIG. 1, a human tissue cell membrane, such as a liver cell or hepatocyte, is diagrammatically shown which contains certain sub-cellular organelles which are specialized parts of a protozoan or tissue cell. These subcellular units include mitochondria, the Golgi apparatus, cell center and centrioles, granular and agranular endoplasmic reticulum, vacuoles, microsomes, lysosomes, plasma membrane, and certain fibrils, as well as plastids of plant cells. Leukocytes and perhaps other rapidly dividing cells are believed to be the primary site of production of the psoriasis molecule (P.M.). Hence it is an object of this invention to biochemically and/or genetically change or reduce the effects of this hideous disease by treating the affected sub-cellular organelles with compounds of nickel and bromide. The key to the invention is to effect transport of the element nickel (Ni) into the cell and sub-cells, such as the mitochondria or Golgi wherein the needful metalloenzymes can catabolize the P.M. into a less toxic and or easier excreted molecule. It is believed the rejection of nickel from entering the cell prevents a biochemical change in the P.M. to a less toxic form. It is believed, as diagrammatically shown, the use of Br with Ni is an effective carrier to overcome this rejection.

Figure 2:
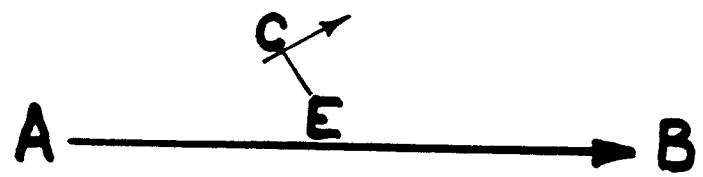
FIG. 2 is a diagrammatic pathway depicting the treatment concepts of the invention.

The drawing of FIG. 2 diagrammatically describes the pathway of treatment of the P.M. (A) to a less toxic catabolic product (B) by treatment of a nickel dependent metalloenzyme (E) located in the sub-cellular organelles. The nickel (Ni)/bromide (Br) of the invention becomes the catalytic lever (C) or switch to activate the metalloenzyme to its maximum function.

One form of the invention is directed to the topical or oral use of nickel dibromide ($NiBr_2$), or $NiBr_2$ hydrate, in adult dosages within the range of 0.037 mg to 370 mg of $NiBr_2$ per dose. As such, this is equivalent to the use of 0.01 mg to 100 mg of Ni per dose. The dosages can be mixed in sucrose or lactose or other appropriate form and can be contained with a gelatin capsule or other appropriate oral vehicle. With children, the pediatric dosage is 0.001 mg to 110 mg of $NiBr_2$ per kg per dose within a purified or distilled water plus any form of pleasant-tasting flavoring (elixir). The dosages can be available for a variety of psoriasis situations, including from once a week or once a month to once or twice daily dosages. In some instances, once a day for 5 to 15 days per month for up to 6 months may be effective. It may be desirable or necessary to provide bromide pre-loading and/or post loading wherein 5 to 500 mg of bromide would be given orally (p.o.) in capsule or elixir in a form such as sodium bromide, potassium bromide, or ammonium bromide or combinations of these which would be given in dosages once daily from 5 to 15 days prior to or after the dosing of $NiBr_2$. In other instances, bromide formulations may be given simultaneously with the $NiBr_2$.

Another process for treatment would include first obtaining a nickel patch test of a patient to determine if there is any contact allergy. To determine effectiveness, pre-treatment color photographs of the psoriasis lesions would be obtained prior to starting. Also pre-treatment serum tests for nickel, bromide, zinc, copper, a complete blood count (CBC), and a sequential multichannel autoanalyzer count (SMAC) would be accomplished. A 90 kg man would ingest 2 mg of nickel as nickel sulfate ($NiSo_4$) and 20 mg of bromide (Br) as sodium bromide (NaBr)/per day. These are mixed together in 15 cc of distilled or purified water and taken once daily p.o. on an empty stomach. This process would be repeated for 21 days. Subsequently, a nickel patch test would be taken at a three-week anniversary, photographs taken weekly after starting the process, and post-treatment serum tests as identified in the pre-treatment tests are repeated.

References and studies indicate that the use of NaBr is within well-recognized safe limits. For example, if 20 mg of bromide by way of NaBr were given orally once a day for 21 days, it would be equivalent to 420 mg given; assuming 100 percent (100%) absorption and an acceptable daily intake (A.D.I.) were 0.4 mg/kg/day. Thus, for a 90 kg adult male, 20 mg of bromide per day is well under the A.D.I. or 35 mg per day. Reference is made to Van Leeuwen, F. X. et al, The Toxicology of Bromide IN; CRC *Critical Reviews in Toxicology,* 18:189–213; (1987). This reference indicates that the dietary intake in the United Kingdom and in the Netherlands is within the range of 2–17 mg per day. There are apparently no studies on the carcinogenicity. Bromide has been given for 140 years without any carcinogenic effect being reported. See Livingston S. et al; Bromides in the Treatment of Epilepsy in Children; *American Journal of Diseases of Children;* 86:717–720; (1953). Likewise, the literature indicates that the quantitative exposure giving a 90 kg adult male 2 mg nickel (Ni) by way of $NiSO_4-6H_2O$ orally and daily for 21 days will equal 42 mg given. This daily dose is approximately two times higher than that recommended for contaminated IV fluids per day and twenty percent (20%) of dose causing increased coronary artery resistance in single IV dose in dogs. Assume five percent (5) of the nickel absorbed would equate to 2.1 mg. Assuming thirty percent (30%) of that which is absorbed is deposited in tissues for a mean retention time of 200 days, 30 micrograms (0.3×100) retained each day for the 21 days would equate to a total of 630 micrograms retained. If the normal body burden of Ni equals 7 micrograms per kg, therefore, approximately 21 days will be required to double body burden of Ni for a 90 kg adult. Reference is made to Sunderman, F. W., Jr.; Potential Toxicity from Nickel Contamination of IV Fluids; *Annals of Clinical and Laboratory Science;* 13:1–4(1983). According to Sunderman, F. W. Sr., regarding the current status of Ni carcinogenesis; *Annals of Clinical and Laboratory Science;* 3–156–180 (1973), "$NiSO_4$ is a 'non-carcinogne'—since it is so highly soluble." Likewise "soluble nickel salts such as nickel chloride, nickel sulfate, and nickel ammoniumsulfate, have not, been shown to be carcinogenic"; Sunderman, F. W. Sr.; A Pilgrimage Into the Archives of Nickel Toxicology; *Annals of Clinical and Laboratory Science;* 19:1–16;(1989). In addition, the dietary intake of nickel averages 300–600 micrograms per day for an average American adult. Sunderman, F. W. Jr.; *A Review of the Metabolism and Toxicology of Nickel*; *Annals of Clinical and Laboratory Science;* 7:377–398; (1977).

Hence, based on the literature and the studies, it would appear that the use of nickel sulfate and sodium bromide can be effectively employed. The bromide may be absorbed topically from bath solutions or other formulations in creams, ointments, or lotions.

An exemplary test includes two psoriatic patients with active skin disease and a healthy control. The test subjects will be immersed in water high in bromide content. The water of the Dead Sea is found to be of that quality. The subject would be immersed, neck down, for 30 minutes every hour for two four-hour sessions daily for a total of ten days. All activities, including bathing, will be done in sun-shaded facilities, and no suntanning will be permitted. Prior to the study, nickel patch testing as above-described is done on all the subjects, and no medications of any type (systemic or topical) will be taken for at least six weeks prior to the study, during the study, and for six weeks after the study. Only bland emollients will be permitted. Nickel sulfate containing 2.5 mg of nickel is administered orally twice daily during the ten-day study at the beginning of each four-hour bathing session. The aforesaid serum and urine level tests for bromide and nickel will be obtained from all test subjects prior to the onset of each treatment day and at the end of the treatment period with similar levels being tested at the end of each week after therapy. The CBC, SMAC, serum zinc, and serum copper levels will be studied at the beginning and the end of the treatment period and at the end of the study, followed by a nickel patch test.

PRELIMINARY STUDY

A preliminary study was conducted in conjunction with a 39 year old white male who had over a 15-year history of difficulty controlling the plaque-type of psoriasis vulgaris. The patient had been treated for approximately five years previously with limited success, with maximum B range ultraviolet rays (UVB), along with topically applied tar, corticosteroids, and 5-fluorouracil. The history of the patient showed active flaring of the plaque type of psoriasis over 20 to 30% of the body surface area which were scaly and thickened. No pustules nor inverse patterns were noted. There was minimal involvement of the disease on the face, and the palms of the hands were spared.

Prior to treatment, the following evaluations were conducted: Nickel patch testing, exercise tolerance testing, serum nickel, bromide, zinc, copper, SMAC, blood CBC drawn, and preliminary photographs of the affected areas were taken.

The solution itself was obtained by mixing together nickel sulfate $(NiSO_4) \cdot 6H_2O$ and Nickel bromide. Nickel dibromide $(NiBr_2)$ resulted in a 5 mg/50 mg ratio of Ni to Br. These were mixed together in purified water to a concentration of 2 mg of Ni and 20 mg of Br per 15 cc of solution. These compounds mixed easily into a colorless solution and were placed in a standard, round, glass pharmacy jar. The compound minerals themselves were ASC grade and purchased from New York City Chemical Corporation. The study comprised the patients' ingestion of very small amounts of the subject solution in order to effect ingestion of 2 mg of nickel and 20 mg of bromide once daily for 21 days. Every seven days standard photos were taken; and on day 21, laboratory tests of serum, nickel, bromide, zinc, copper, SMAC, and blood CBC were conducted. The ingestion by the patient was to be conducted on an empty stomach. Following the treatment, a nickel patch test was conducted along with standard photographs at one-week, three-week, and five-week intervals, with tests for serum nickel and bromide at three weeks post treatment.

During the three-week course of therapy, the following results were noted:

1. No new psoriatic lesions (plaques) were noted at one week and two weeks into therapy. There was a very rare new papule noted at three weeks into therapy. This is a positive result, especially when considered in the setting of rapidly flaring disease prior to the initiation of this treatment and since this patient was in the midst of some severe domestic stresses during the treatment period. Stress has been considered a factor in triggering psoriasis lesions.

2. The existing lesions became less scaly and less reddened and thinner during the entire treatment course. The periphery (circumference) enlarged minimally, and small areas of more normal appearing skin appeared in their centers during treatment.

3. One area on the central chest showed more pronounced clearing than any of the rest of the lesions. There was approximately 50% complete clearing in this area.

At three weeks post-treatment, i.e. the patient was completely off treatment for three weeks, there was noticeable worsening on all the above parameters (new lesions forming, existing lesions turning more bright red in color and producing more bothersome scaly buildup, and all lesions thickening notably).

The above findings are felt to reflect favorable effects of the study medication on the test patient's skin.

MODIFICATIONS

Although certain specific forms of nickel and bromide compounds are set forth herein, other pharmaceutically acceptable compounds are inclusive of the invention, e.g. Nickel Sulfate $(NiSO_4)$, Nickel Chloride $(NiCl_2)$, Sodium Bromide (NaBr), Potassium Bromide (KBr) and Ammonium Bromide $(NH_4Br)$.

In many instances pre, during, and/or post treatment will include topical and/or systemic (oral) or intravenous use of anti-bacterial compounds, e.g. penicillin, and anti-fungal agents, e.g. Ketoconazole.

What is claimed:

1. A method of treating human being for psoriasis comprising the step of orally administering a psoriasis inhibiting effective amount of a formulation containing a non-toxic, pharmaceutically acceptable nickel (Ni) salt(s) in a human patient, and dosing the patient such that said formulation provides an amount of nickel from about 2 to about 300 mcg/kg of patient weight/day is administered.

2. The method of claim 1 including the step of treating said human being with anti-bacterial agents.

3. The method of claim 1 including the step of treating said human being with anti-fungal agents.

4. The method of claim 1 including the step of treating said human being with anti-bacterial and anti-fungal agents.

5. The method of claim 1 further comprising administering said formulation in aqueous form.

6. The method of claim 1 further comprising administering said formulation in tablet or capsule form.

7. A method of treating human patient for psoriasis comprising the step of orally administering an aqueous or saline solution containing a psoriasis inhibiting effective amount of pharmaceutically acceptable amounts of nickel (Ni) in said human patient, said Ni being derived from a non-toxic, pharmaceutically acceptable nickel salt, and dosing said human patient such that an amount of nickel from about 2 to about 300 mcg/kg of patient weight/day is administered.

8. The method of claim 7 wherein said Ni is derived from a Ni salt(s) selected from the group consisting of $NiBr_2$, $NiSO_4$, $NiCl_2$ and mixtures thereof.

9. The method of claim 7 including the step of treating said human being with anti-bacterial agents.

10. The method of claim 7 including the step of treating said human being with anti-fungal agents.

11. The method of claim 7 including the step of treating said human being with anti-bacterial and anti-fungal agents.

12. A method of catabolizing a psoriasis molecule (P.M.) residing in a human being into a less toxic and excretable molecule comprising the step of introducing a psoriasis inhibiting effective amount of nickel (Ni) derived from a pharmaceutically acceptable Ni salt(s) into sub-cellular organelles containing said P.M., and administering a dose of Ni from about 2 to about 300 mcg/kg of patient weight/day to a human patient.

13. A method of catabolizing a psoriasis molecule (P.M.) residing in a human being into a less toxic and/or excretable molecule comprising the step of introducing a psoriasis inhibiting effective amount of nickel (Ni) into sub-cellular organelles containing said P.M., and introducing the Ni into the human patient as an oral dose of $NiBr_2$ in an aqueous or saline solution in an amount from about 2 to about 300 mcg/kg of patient weight/day to a human patient.

14. The method of claim 7 wherein said Ni is derived from $NiBr_2$ in an aqueous or saline solution vehicle.

15. The method of claim 14 wherein said solution is introduced internally into said patient orally in daily amounts such that said patient ingests from about 5 to 150 mcg Ni/kg of patient weight/per day.

16. The method of claim 7 wherein said vehicle further comprises a bromide selected from the group of pharmaceutically acceptable NaBr, KBr and $NH_4Br$.

17. A method of treating human beings for psoriasis comprising the step of orally administering a psoriasis inhibiting effective amount of pharmaceutically acceptable amounts of nickel bromide ($NiBr_2$) to a human patient, and dosing the human patient such that an amount of nickel from about 2 to about 300 mcg/kg of patient weight/day is administered.

18. A method of treating human being for psoriasis comprising the step of orally administering a psoriasis inhibiting effective amount of nickel (Ni) derived from a pharmaceutically acceptable nickel salt(s) in combination with a non-toxic, pharmaceutically acceptable bromide salt, and providing a dose of Ni from about 2 to about 300 mcg/kg of patient weight/day.

19. The method of claim 18, wherein said bromide salt is selected from the group consisting of group of $NiBr_2$, NaBr, KBr, $NH_4Br$, and mixtures thereof.

20. The method of claim 1 wherein said formulation provides an amount of nickel from about 5 to about 150 mcg/kg of patient weight/day.

21. The method of claim 1 wherein said formulation provides an amount of nickel from about 5 to about 50 mcg/kg of patient weight/day.

22. The method of claim 17, wherein said formulation provides an amount of nickel from about 5 to about 150 mcg/kg of patient weight/day.

23. The method of claim 17, wherein said formulation provides an amount of nickel from about 5 to about 50 mcg/kg of patient weight/day.

* * * * *